United States Patent
Oya et al.

(10) Patent No.: US 7,812,623 B2
(45) Date of Patent: *Oct. 12, 2010

(54) TRANSPARENT CONDUCTIVE FILM ROLL AND PRODUCTION METHOD THEREOF, TOUCH PANEL USING THE SAME, AND NON-CONTACT SURFACE RESISTANCE MEASURING DEVICE

(75) Inventors: Toshiyuki Oya, Otsu (JP); Hideo Murakami, Otsu (JP); Chikao Morishige, Otsu (JP); Yuji Kakita, Otsu (JP); Hideki Jinbou, Otsu (JP); Kenjiro Ueda, Otsu (JP); Takahiro Kubota, Otsu (JP)

(73) Assignee: Toyo Boseki Kabushiki Kaisha, Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/212,177

(22) Filed: Sep. 17, 2008

(65) Prior Publication Data
US 2009/0039878 A1   Feb. 12, 2009

Related U.S. Application Data

(63) Continuation of application No. 10/481,235, filed as application No. PCT/JP02/05871 on Jun. 13, 2002, now Pat. No. 7,436,190.

(30) Foreign Application Priority Data

Jun. 21, 2001  (JP)  ............................. 2001-188556
Oct. 17, 2001  (JP)  ............................. 2001-319735

(51) Int. Cl.
*G01R 31/302*   (2006.01)

(52) U.S. Cl. ..................................... 324/750; 324/158.1
(58) Field of Classification Search ....................... None
See application file for complete search history.

(56) References Cited

U.S. PATENT DOCUMENTS

| 4,571,350 | A   | * | 2/1986  | Parker et al.    | ................ | 427/109 |
| 6,284,393 | B1  | * | 9/2001  | Hosokawa et al.  | ................ | 428/690 |
| 6,611,299 | B1  | * | 8/2003  | Fujii et al.     | ................ | 349/12  |
| 6,629,833 | B1  |   | 10/2003 | Ohya et al.      |                  |         |

(Continued)

FOREIGN PATENT DOCUMENTS

JP     61120961 A     6/1986

(Continued)

OTHER PUBLICATIONS

Japan Patent Office; Notice of Reasons for Refusal dated Mar. 7, 2006 in Japanese Application No. JP2002-181972.

*Primary Examiner*—Minh N Tang
(74) *Attorney, Agent, or Firm*—Kenyon & Kenyon LLP

(57) ABSTRACT

A transparent conductive film roll which has a transparent conductive layer on at least one surface thereof and has an excellent distribution uniformity of surface resistance in longitudinal and lateral directions thereof wherein the distribution uniformity D of surface resistance defined by the following expression (1) is 0.2 or less when the surface resistance of the transparent conductive layer is measured at a total of 33 points within the film roll, and therefore, is suitable especially for a large panel, $$D=(R{max}-R{min})/(R{max}+R{min}) \quad (1)$$

where Rmax and Rmin represent the maximum and minimum values of 33 surface resistance measurement values.

4 Claims, 7 Drawing Sheets

3-Eddy current sensor
4A-Temperature sensor
4B-Separation distance sensor
6-Sensor amplifier
7-Computer
8-CRT
9-Printer
10-Alarm device

U.S. PATENT DOCUMENTS 7,436,190 B2 * 10/2008 Oya et al. .................. 324/750

FOREIGN PATENT DOCUMENTS

| JP | 03-122910 | 5/1991 |
| JP | 06-103840 | 4/1994 |
| JP | 06-275132 | 9/1994 |
| JP | 09-161542 | 6/1997 |
| JP | 10-036967 | 1/1998 |
| JP | 116777 A | 1/1999 |
| JP | 11-034207 | 2/1999 |
| JP | 2000-108241 | 4/2000 |
| JP | 2000-230950 | 8/2000 |
| JP | 2000-265259 | 9/2000 |

* cited by examiner

3-Eddy current sensor
4A-Temperature sensor
4B-Separation distance sensor
6-Sensor amplifier
7-Computer
8-CRT
9-Printer
10-Alarm device

TRANSPARENT CONDUCTIVE FILM ROLL AND PRODUCTION METHOD THEREOF, TOUCH PANEL USING THE SAME, AND NON-CONTACT SURFACE RESISTANCE MEASURING DEVICE This is a continuation application of U.S. patent application Ser. No. 10/481,235 filed on 30 Jul. 2004, now U.S. Pat. No. 7,436,190, which is a 371 national phase application of PCT/JP02/05871 filed on 13 Jun. 2002, claiming priority to JP 2001-188556, filed on 21 Jun. 2001, and JP 2001-319735 filed on 17 Oct. 2001, the contents of which are incorporated herein by reference in their entirety.

TECHNICAL FIELD

The present invention relates to a transparent conductive film roll which is a roll of transparent conductive film, in which a transparent conductive layer is laminated on a plastic film, and a production method thereof, and a touch panel using the same and a non-contact surface resistance measuring device. More particularly, the present invention relates to a long transparent conductive film roll having a uniform surface resistance distribution in a longitudinal direction thereof and in a lateral direction thereof, which is suitable for a transparent electrode for a touch panel or an electroluminescence panel which requires transparency and conductivity, particularly a transparent electrode for a large panel, and a touch panel using the same and a non-contact surface resistance measuring device.

BACKGROUND ART

As a transparent conductive film, a film comprising a plastic film and a conductive material provided thereon is commonly used. As the conductive material, either organic or inorganic materials can be used. Inorganic materials are preferable in terms of both conductivity and transparency. As the inorganic material, metals, such as gold, silver and the like, and metal oxides are preferable in terms of transparency. Among metal oxides, indium oxide, tin oxide, zinc oxide, and mixed oxides thereof are particularly preferable. Films in which the above-described metal oxide is deposited on a plastic film using a vapor deposition method, an ion plating method, a sputtering method or a CVD method, are known.

Transparent conductive films are generally produced by an ion plating device or a sputtering device which roll up a film. A transparent conductive film roll produced by the above-described device is cut by a slitter into pieces having a size of about 300 to 800 mm in width and about 10 to 1000 m in length, which are in turn rolled up by a paper tube or plastic core. Thus, the transparent conductive film is generally circulated in the form of a film roll. After a film roll in which a film is rolled up is cut into sheets, silver paste printing, dielectric printing or the like is performed on the film so that the resultant film is used as a transparent electrode for a tough panel or an electroluminescence panel.

In analog touch panels, the position of an input is recognized and characters or symbols are displayed, assuming that the distribution of surface resistance of a transparent electrode thereof is uniform ("Gekkan Disupurei [Monthly Display", September 1999, p. 82). Therefore, the surface resistance of a transparent conductive film used therein needs to be uniformly distributed at any position thereof. Also, in the case of transparent electrodes of electroluminescence panels, a transparent electrode having a uniform surface resistance distribution is required to obtain uniform light emission intensity within the panel. In particular, as the size of an electroluminescence panel is increased, the higher degree of uniformity is required for the distribution of surface resistance of a transparent electrode thereof.

The distribution of surface resistance of a transparent electrode can be made uniform as follows. A surface resistance measuring device is provided in a rolled-up film forming device. The surface resistance of a transparent conductive layer is sequentially measured in-line while forming the transparent conductive layer. Conditions for forming the transparent conductive layer are regulated so that the surface resistance thereof is uniformly distributed.

An example of the above-described method includes a method for contacting and sandwiching a transparent conductive film between two metal rollers and measuring the surface resistance between the rollers. However, in principle, this method can measure the distribution of surface resistance of a transparent conductive film in a longitudinal direction thereof, but not the surface resistance distribution in a lateral direction thereof. Concerning the surface resistance distribution in a longitudinal direction thereof, if the tension of the film is not uniform, the contact between the metal rolls and the transparent conductive layer is not uniform, leading to errors in the measurement of the surface resistance.

There is also a method for measuring the surface resistance of a transparent conductive film in a lateral direction thereof, in which three or more metal rings are provided around an insulated roller (made of silicone rubber or polytetrafluoroethylene) and the resistance between each metal ring is measured. However, a small protrusion is formed between the insulator and the metal ring, which is likely to damage the film surface.

Therefore, as a surface resistance measuring device which can sequentially measure the surface resistance distribution in a lateral direction thereof and does not damage the film surface, a method for measuring a coupled inductance between an electromagnetic induction coil and a conductive film (a method for applying magnetic field and measuring a resulting eddy current) is known ("Gekkan Disupurei [Monthly Display", September 1999, p. 88). In this method, however, a considerably high intensity of applied magnetic field is required for the measurement of a conductive film having a surface resistance of 10 Ω/□ or more. In this case, the spread of magnetic flux is large, leading to the path line fluctuation of a substrate in a production process (vibration in a direction normal to a surface of the substrate). Thus, a distance between a sensor section and a conductive film to be measured fluctuates and the coupled inductance is not constant. As a result, the in-line sequential measurement has large measurement errors.

Further, in this method, the magnetic permeability of a ferrite coil which functions as an eddy current generating section or an eddy current detecting section has a temperature dependency. The inductance is changed in accordance with, if any, the fluctuation of the temperature. Therefore, even if a high frequency voltage applied to the coil is constant, an eddy current flowing through the conductive film is changed, resulting in large measurement errors.

As described above, even if a general surface resistance measuring device is provided in a rolling up device, large measurement errors make it considerably difficult to obtain a transparent conductive film roll having uniform surface resistance.

The present invention was made, taking the above-described circumstances into consideration. An object of the present invention is to provide a transparent conductive film roll having a uniform surface resistance distribution in a longitudinal direction thereof and in a lateral direction thereof; a production method thereof; and a touch panel produced using the same.

DISCLOSURE OF THE INVENTION

A transparent conductive film roll of the present invention is obtained by rolling up a plastic film having a transparent conductive layer on at least one side thereof. A width thereof is 300 to 1300 mm and a length thereof is 10 to 1000 m. When the surface resistance (Ω/~) of the transparent conductive layer is measured at a total of 33 points including positions located at a middle in a lateral direction thereof and any positions located at a distance of from 25 to 100 mm from lateral ends thereof, the positions being separated in intervals of $1/10$ of a full length in a longitudinal direction thereof, the distribution uniformity D of the surface resistance is 0.20 or less. The distribution uniformity D is represented by expression (1):

$$D=(R\max-R\min)/(R\max+R\min) \quad (1)$$

where Rmax and Rmin represent the maximum and minimum surface resistance values measured at the 33 points, respectively. The closer to zero the distribution uniformity D of the surface resistance, the smaller the fluctuation of the surface resistance.

A touch panel of the present invention comprises a pair of panel plates having a transparent conductive layer. The panel plates are disposed via a spacer so that the transparent conductive layers face each other. At least one of the panel plates is a transparent conductive film obtained by cutting the above-described transparent conductive film roll.

A method of the present invention is provided for producing a transparent conductive film roll having a transparent conductive layer on at least one side thereof using a rolled-up film forming device. The rolled-up film forming device has anon-contact surface resistance measuring device therewithin. The surface resistance of the transparent conductive layer is sequentially measured in line at a plurality of position in each of longitudinal and lateral directions of the film while forming the transparent conductive layer. Conditions for forming the transparent conductive layer are regulated so that the surface resistance thereof is uniformly distributed. The non-contact surface resistance measuring device of the present invention mainly comprises an eddy current generating section which is placed at a predetermined distance from the transparent conductive layer, faces the transparent conductive layer and flows an eddy current in the transparent conductive layer, an eddy current detecting section which is separated from the transparent conductive layer and detects the eddy current flowing through the transparent conductive layer, a temperature detecting section which detects a temperature of the eddy current generating section or the eddy current detecting section, and a calculating means which calculates a surface resistance of the transparent conductive layer based on a result of detection by the eddy current detecting section and a result of detection by the temperature detecting section where a voltage applied to the eddy current generating section is constant. When the result of detection by the temperature detecting section is deviated from a reference temperature, the calculating means calculates an amount of an increase or decrease in the eddy current caused by the deviation from the reference temperature and adds or subtracts the amount of the increase or decrease in the eddy current to or from the result of detection by the eddy current detecting section to correct the value of the eddy current and calculates the surface resistance of the transparent conductive layer based on the corrected value of the eddy current.

A non-contact surface resistance measuring device of the present invention mainly comprises an eddy current generating section which is placed at a predetermined distance from the transparent conductive layer, faces the transparent conductive layer and flows an eddy current in the transparent conductive layer, an eddy current detecting section which is separated from the transparent conductive layer and detects the eddy current flowing through the transparent conductive layer, a temperature detecting section which detects a temperature of the eddy current generating section or the eddy current detecting section, and a calculating means which calculates a surface resistance of the transparent conductive layer based on a result of detection by the eddy current detecting section and a result of detection by the temperature detecting section where a voltage applied to the eddy current generating section is constant. When the result of detection by the temperature detecting section is deviated from a reference temperature, the calculating means calculates an amount of an increase or decrease in the eddy current caused by the deviation from the reference temperature and adds or subtracts the amount of the increase or decrease in the eddy current to or from the result of detection by the eddy current detecting section to correct the value of the eddy current and calculates the surface resistance of the transparent conductive layer based on the corrected value of the eddy current.

The plastic film used as the substrate for the transparent conductive film roll of the present invention is obtained by extruding an organic polymer in a molten or solution state and optionally stretching the polymer in a longitudinal and/or lateral directions thereof, cooling and annealing the polymer.

Examples of such an organic polymer include polyethylenes, polypropylenes, polyethylene terephthalates, polyethylene-2,6-naphthalates, polypropylene terephthalates, nylon 6, nylon 4, nylon 6.6, nylon 12, polyimides, polyamideimides, polyethersulfanes, polyetheretherketones, polycarbonates, polyarylates, cellulose propionates, polyvinyl chlorides, polyvinylidene chlorides, polyvinyl alcohols, polyetherimides, polyphenylene sulfides, polyphenylene oxides, polystyrenes, syndiotactic polystyrenes, norbornene polymers, and the like.

Among these organic polymers, polyethylene terephthalates, polypropylene terephthalates, polyethylene-2,6-naphthalates, syndiotactic polystyrenes, norbornene polymers, polycarbonates, polyarylates, and the like are preferable. These organic polymers may be used as homopolymer or may be copolymerized with a small amount of monomers of other organic polymers. Also, these organic polymers may be blended with one or more kinds of other organic polymers.

The above-described plastic film needs to have an excellent level of transparency in view of the visibility of a panel. Therefore, it is preferable that particles, additives or the like which worsen the transparency are not contained in the plastic film. However, the film surface preferably has an appropriate level of surface roughness in view of handling ability (sliding ability, running ability, blocking ability, ability to purge accompanying air when rolling up, etc.) in producing a plastic film and unrolling or rolling a roll.

To meet mutually contradictory characteristics, a substrate film having a layered structure is produced by a coating method or coextruding method, where the thickness of the film is considerably small, i.e., 0.03 to 1 μm and particles are contained only in a surface layer. Among these methods, the coating method is preferable. This is because the coating method can produce a film thinner than that made by the coextruding method, so that the adhesion between the plastic film and a conducting layer can be satisfactory.

When a layered plastic film is used as a substrate, one or more kinds of particles may be contained in a surface layer thereof. Particles having a refractive index equal or close to that of a component resin of the plastic film and a binder resin of a coat layer thereof are preferable in view of the transparency thereof. For example, when a polyester-based resin is used as a binder resin in the substrate or the coat layer, 0.5 to 5.0% by weight of particles (e.g., silica, glass filler, mixed oxide such as alumina-silica, etc.) having an average diameter of 10 to 200 nm are preferably contained in the binder resin.

The thickness of the plastic film is preferably in the range of more than 10 μm and no more than 300 μm, particularly preferably in the range of from 70 to 260 μm. When the thickness of the plastic film is no more than 10 μm, the mechanical strength is insufficient. In this case, particularly, when the plastic film is used in a touch panel, the film is likely to be significantly deformed by a stylus input, resulting in insufficient durability. When the thickness exceeds 300 μm, it is difficult to roll up the film.

The surface of the above-described plastic film may be subjected to surface activating treatment, such as corona discharge treatment, glow discharge treatment, flame treatment, ultraviolet irradiation treatment, electron beam irradiation treatment, ozone treatment, or the like, to an extent which does not impair the object of the present invention.

A curable resin cured material layer or an inorganic thin film layer may be provided between the substrate plastic film and the transparent conductive layer so as to improve the adhesiveness of the transparent conductive layer. The curable resin may not be particularly limited as long as the resin is capable of being cured by applying energy, such as heating, ultraviolet irradiation, electron beam irradiation, or the like. Examples of the curable resin include silicone resins, acrylic resins, methacrylic resins, epoxy resins, melamine resins, polyester resins, urethane resins, and the like. An ultraviolet curable resin is preferably a major component in view of productivity.

The transparent conductive layer used in the present invention is not particularly limited as long as the transparent conductive layer is made of a material having both transparency and conductivity. Examples of the transparent conductive layer include a monolayer structure or a layered structure having two or more layers, which are made of indium oxide, tin oxide, zinc oxide, indium-tin mixed oxides, tin-antimony mixed oxides, zinc-aluminum mixed oxides, indium-zinc mixed oxides, silver and silver alloys, copper and copper alloys, gold, or the like. Among them, indium-tin mixed oxides or tin-antimony mixed oxides are preferable in view of environmental stability or circuit workability.

In order to adjust the surface resistance or the transparency, the transparent conductive layer may contain at least one of titanium oxide, cerium oxide, tungsten oxide, niobe oxide, yttrium oxide, zirconium oxide, silicon oxide, zinc oxide, gallium oxide, aluminum oxide, antimony oxide, tantalum oxide, hafnium oxide, samarium oxide, and the like. The total amount of the inorganic oxide contents is preferably 10% by weight or less with respect to the major component of the transparent conductive layer.

The thickness of the transparent conductive layer is preferably in the range of from 4 to 800 nm, particularly preferably from 5 to 500 nm. When the transparent conductive layer has a thickness of less than 4 nm, it is difficult to produce a continuous thin film and the transparent conductive layer tends not to have a satisfactory level of conductivity. When the thickness is more than 800 nm, the transparency is likely to be reduced.

Examples of a known method for forming a transparent conductive layer of the present invention include a vacuum deposition method, a sputtering method, a CVD method, an ion plating method, a spraying method, and the like. Among these methods, an appropriate method may be selected depending on a required thickness.

Examples of the sputtering method include a typical sputtering method using an oxide target, a reactive sputtering method using a metal target, and the like. In this case, a reactive gas, such as oxygen, nitrogen or the like, may be introduced, or a technique, such as ozone addition, plasma irradiation, ion assist or the like, may be used in combination with the sputtering method. A bias, such as direct current, alternating current, high frequency or the like, may be applied to the substrate to such an extent that the object of the present invention is not impaired.

A monolayer or a multilayer made of a material having a refractive index different from that of the transparent conductive layer may be preferably provided between the transparent conductive layer and the plastic film so as to reduce the light reflectance of the transparent conductive film at a surface of the transparent conductive layer and improve the light transmittance thereof. In the case of the monolayer, a material having a refractive index smaller than that of the transparent conductive layer is preferably used. In the case of a multilayered structure having two or more layers, a layer adjacent to the plastic film may be made of a material having a refractive index greater than that of the plastic film while a layer underlying the transparent conductive layer may be made of a material having a refractive index smaller than that of the transparent conductive layer.

The above-described material for low reflection treatment is not particularly limited to organic or inorganic materials as long as the material satisfies the above-described relationship between the refractive indexes. Examples of the material include dielectric materials, such as $CaF_2$, $MgF_2$, $NaAlF_4$, $SiO_2$, $ThF_4$, $ZrO_2$, $Nd_2O_3$, $SnO_2$, $TiO_2$, $CeO_2$, $ZnS$, $In_2O_3$, and the like.

A transparent conductive film roll of the present invention has a uniform surface resistance distribution in longitudinal and lateral directions thereof, where a distribution uniformity D of the surface resistance is 0.20 or less, the distribution uniformity D being represented by expression (1):

$$D=(Rmax-Rmin)/(Rmax+Rmin) \qquad (1).$$

In a transparent conductive film roll produced by the above-described material and method, the surface resistance distribution is made uniform in longitudinal and lateral directions thereof by using an in-line and non-contact surface resistance measuring device described below which is provided in a rolled-up film forming device in the step of providing a transparent conductive layer.

A configuration of the non-contact surface resistance measuring device will be described with reference to FIG. 1.

The non-contact surface resistance measuring device comprises a plurality (n) of eddy current sensors 3 which are placed at a predetermined distance from a conductive layer 2 on a substrate 1 and faces the conductive layer 2. The eddy current sensor 3 comprises an eddy current generating section which flows an eddy current in the conductive layer 2, and an eddy current detecting section (integrated with the eddy current generating section of the eddy current sensor 3) which is separated from the conductive layer 2 and detects the eddy current flowing through the conductive layer 2. A temperature sensor 4A (corresponding to a temperature detecting section) which detects a temperature of the eddy current sensor 3 and a separation distance sensor 4B which detects the distance between the eddy current sensor 3 and the conductive layer 2 are integrated with the eddy current sensor 3. The non-contact surface resistance measuring device further comprises a computer 7 (corresponding to a calculation means) which calculates the surface resistance of the conductive layer 2 based on the results of detection by the eddy current detecting section of the eddy current sensor 3 and the results of detection by the temperature sensor 4A and the separation distance sensor 4B.

The eddy current sensor 3, the temperature sensor 4A and the separation distance sensor 4B are each connected to a sensor amplifier 6. The sensor amplifier 6 comprises a high frequency oscillator, an A/D converting means which converts an analog signal of an eddy current to a digital signal, an A/D converting means which converts an analog signal corresponding to a separation distance between the conductive layer 2 and the sensor 3 to a digital signal, and an A/D converting means which converts an analog signal corresponding to a temperature to a digital signal. The high frequency oscillator applies a high frequency to the conductive layer and detects an eddy current flowing through the conductive layer.

Preferably, the separation distance sensor 4B which detects a separation distance between the conductive layer 2 and the sensor 3 is a displacement sensor of capacitance type, ultrasonic type, laser type, photoelectric type or the like. The means which calculates the surface resistance of a conductive layer is based on a digital signal.

A method of flowing an eddy current in a conductive layer is achieved by providing an eddy current generating section and an eddy current detecting section so that they are located a predetermined distance from the conductive layer and face the conductive layer, or by sandwiching the conductive film by an eddy current generating section and an eddy current detecting section. For example, a high frequency voltage is applied to a coil, such as a ferrite coil or the like, which functions as an eddy current generating section, and the coil is moved close to a conductive layer, or a conductive film is sandwiched by the coil to flow an eddy current in the conductive layer due to high frequency inductive coupling.

When a high frequency voltage is constant, an eddy current flowing in the conductive layer is inversely proportional to the surface resistance of the conductive layer. Therefore, if a calibration curve is previously provided for a relationship between eddy current and surface resistance, a surface resistance can be obtained at a separation distance (reference point).

In principle, an eddy current tends to be decreased with an increase in a separation distance between a conductive layer and a sensor. A pre-prepared calibration curve is provided for a relationship between eddy current and a separation distance. Specifically, a means which detects the separation distance between a conductive layer and a sensor is used to obtain a separation distance. A difference between the separation distance and a reference point is obtained. A correction value is calculated for an eddy current based on the calibration curve. The correction value is subtracted when the separation distance between a conductive layer and a sensor is smaller than the reference point, while the correction value is added when the separation distance between a conductive layer and a sensor is greater than the reference point. Thus, the surface resistance of a conductive layer can be accurately calculated at any separation distance between the conductive layer and a sensor. The calculation of the surface resistance of a conductive layer is sequentially performed in a production process of the conductive layer in accordance with the operation cycles of a computer.

In principle, the magnetic permeability of a coil which functions as an eddy current generating section or an eddy current detecting section has a temperature dependency. Therefore, an eddy current is changed in accordance with, if any, temperature fluctuation. There is a positive correlation between eddy current and magnetic permeability. There are both positive and negative temperature dependencies of the magnetic permeability of a coil depending on the type of the coil material. Specifically, the positive dependency means that the magnetic permeability is increased with an increase in the temperature. The negative dependency means that the magnetic permeability is decreased with an increase in the temperature.

Therefore, when the result of detection by the temperature sensor 4A is deviated from the reference temperature, the calculating means obtains the amount of an increase or decrease in an eddy current caused by the deviation from the reference temperature based on the temperature dependency of a selected coil material. In addition, the amount of an increase or decrease in the eddy current is subtracted from or added to the detection result by the eddy current detecting section of the eddy current sensor 3 to correct the value of the eddy current. The surface resistance is calculated based on the corrected value of the eddy current.

In this case, it is important to previously prepare a calibration curve for a relationship between temperature fluctuations and corrected eddy current amounts.

Thus, the surface resistance of a conductive layer is calculated based on a previously prepared calibration curve. Therefore, even when the temperature of an eddy current generating section fluctuates, an error is unlikely to occur in the measurement value of the surface resistance of a conductive layer.

By providing a plurality of eddy current generating sections and eddy current detecting sections in a lateral direction of a conductive layer in a production process thereof, the surface resistance of the conductive layer in the lateral direction can be accurately measured even if there is a temperature distribution (uneven temperature) in the lateral direction due to the large width.

The eddy current sensor 3, the temperature sensor 4A and the separation distance sensor 4B are connected via a sensor cable 5 to the sensor amplifier 6. A CRT 8 which displays a measurement result, a printer 9 which produces printed outputs of the measurement result, and an alarm device 10 which reports to an operator that a measured surface resistance exceeds a predetermined range, or an abnormality, are provided.

The sensor amplifier 6 is provided with a high frequency oscillator, a first A/D converter which converts an analog signal of an eddy current to a digital signal, and a second A/D converter which converts an analog signal corresponding to the temperature to a digital signal.

The computer 7 processes data based on digital signals obtained by the first and second A/D converters. When a detection result of the temperature sensor 4A is deviated from the reference temperature, the computer 7 obtains the amount of an increase or decrease in an eddy current caused by the deviation from the reference temperature, adds or subtracts the amount of the increase or decrease in the eddy current to or from a detection result of the eddy current detecting section of the eddy current sensor 3 to correct the value of the eddy current, and calculates the surface resistance of the conductive layer 2 based on the corrected value of the eddy current. This calculation method will be described in detail below.

In a production process for the conductive layer 2, a plurality of non-contact surface resistance measuring devices are provided in a lateral direction of the conductive layer 2 or the non-contact surface resistance measuring device is continuously reciprocated in the lateral direction of the conductive layer 2. Thereby, a surface resistance distribution in the lateral direction of the conductive layer 2 of a transparent conductive film roll or a trend (changes over time) of the surface resistance in a longitudinal direction of the conductive layer 2 can be obtained by the computer 7.

Next, an operation of the non-contact surface resistance measuring device will be described below.

(1) The eddy current sensor 3, the temperature sensor 4A and the separation distance sensor 4B are placed such that the eddy current generating sections of the eddy current sensor 3 faces the conductive layer 2 on the substrate 1 at a predetermined distance of several millimeters from the conductive layer 2, or such that the eddy current generating sections of the eddy current sensor 3 sandwich the substrate 1.

(2) A high frequency is applied from the sensor amplifier 6 to the eddy current generating section of the eddy current sensor 3 to generate an eddy current in the conductive layer 2 due to high frequency induction coupling.

(3) When the applied high frequency voltage is controlled to be constant, an eddy current flowing in the conductive layer 2 is inversely proportional to the surface resistance of the conductive layer 2. Therefore, if a calibration curve is previously provided for a relationship between eddy current and surface resistance as shown in FIG. 2, a surface resistance of an unknown conductive layer 2 can be obtained at the reference temperature where the conductive layer 2 and the eddy current generating section of the eddy current sensor 3 are separated at the predetermined distance.

(4) An eddy current is increased if the temperature dependency of a coil material is a positive dependency. Thus, a surface resistance tends to be small. Therefore, the detection result of the eddy current detecting section of the eddy current sensor 3 is corrected based on the previously prepared calibration curve for the relationship between surface resistance and temperature as shown in FIG. 3.

The correction method will be described in detail below.

For example, it is assumed that a conductive layer has a surface resistance of 50 Ω/□ at a reference temperature of 25° C. If the temperature is increased to 30° C., the surface resistance is about 40 Ω/□, so that the measured value is decreased by 20% from the actual surface resistance. This relationship is represented by expression (2) below.

$$Y=-0.0458X^2+0.2404X+72.9 \quad (2)$$

where the X axis represents ambient temperature (° C.) and the Y axis represents the measured value of the surface resistance (Ω/□).

For example, if 30(° C.) is substituted for X in expression (2), Y is calculated to be 38.9 (Ω/□). A surface resistance is 50 Ω/□ at a reference temperature of 25° C. Therefore, a correction amount is 11.1 Ω/□. The correction amount is added to Y, resulting in a measurement result of 50 Ω/□.

Conversely, if an ambient temperature is decreased to 20° C., 20(° C.) is substituted for X in expression (2). In this case, Y=59.4 (Ω/□). Therefore, a correction amount is 9.4 Ω/□. The correction amount is subtracted from Y, resulting in a measurement result of 50 Ω/□.

The addition and subtraction of a correction amount are previously determined depending on the temperature dependency of a material for a conductive layer. With this correction technique, an error in surface resistance measurement can be reduced even if temperature fluctuates.

Thus, an accurate correction value can be obtained by previously preparing a calibration curve as shown in FIG. 3 for the conductive layer 2 having known surface resistance.

(5) A surface resistance tends to be decreased with an increase in the separation distance between the eddy current sensor and the conductive layer. The calculation result obtained in (4) is corrected based on a calibration curve for the relationship between surface resistance and separation distance shown in FIG. 4.

The surface resistance of the conductive layer 2 is displayed on the CRT 6 by the computer 7 using any software. The surface resistance is used as a measured value or a graph in data processing. The surface resistance is sequentially measured in line. The surface resistance is optionally printed out by the printer 9.

The calculation of the surface resistance of the conductive layer 2 can be sequentially performed in a production process of the conductive layer 2 in accordance with the operation cycles of the computer 7.

By feeding the measurement result of the surface resistance back to the alarm device 10 or a production process, the surface resistance can be controlled in production of a transparent conductive film roll. Thereby, the quality and productivity in production process can be improved.

By integrating the eddy current sensor 3, the temperature sensor 4A and the separation distance sensor 4B together, the eddy current and the temperature can be measured at substantially the same point. Thereby, measurement accuracy can be improved.

Other preferred embodiments of the non-contact surface resistance measuring device will be described below.

In a small production device in which the width of the conductive layer 2 is from about 300 to 500 mm during a production process, a temperature distribution (uneven temperature) in a lateral direction is relatively small and it is considered that temperature fluctuation occurs substantially uniformly. When such a small production device is used to produce the conductive layer 2, it is possible that only a single temperature sensor 4A is provided for a plurality of eddy current sensors 3.

Specifically, the number of the temperature sensors 4A is made smaller than the number of the eddy current generating sections of the eddy current sensor 3, thereby making it possible to suppress the cost of the temperature sensor 4A to a low level.

It is preferable that the temperature sensor 4A has a high resolution and a satisfactory level of accuracy or responsiveness. If the resolution is 0.2° C. or less and the accuracy is ±3% or less, a more accurate measurement result can be obtained.

The eddy current sensor 3 and the temperature sensor 4A may be provided separately. The eddy current generating section of the eddy current sensor 3 and the eddy current detecting section of the eddy current sensor 3 may be provided separately and the eddy current generating section of the eddy current sensor 3 is provided on the side of the conductive layer 2 while the eddy current detecting section of the eddy current sensor 3 and the temperature sensor 4A are provided on the side of the substrate 1.

If a calibration curve is drawn based on data measured in the range of from 10° C. to 40° C. in 1° C. steps, a more accurate result can be obtained, though a temperature range used for correction is not limited to the values described in the embodiments. It is preferable to previously prepare a calibration curve indicating a relationship between surface resistance and temperature for each product sample.

The temperature sensor 4A can be composed of a temperature sensor, such as a thermocouple sensor, a resistance sensor, a thermocouple, an infrared sensor or the like.

As the computer 7, a panel computer, a personal computer, a factory computer or the like can be used.

The numbers of the eddy current generating sections of the eddy current sensor 3, the eddy current detecting sections of the eddy current sensor 3 and the temperature sensors 4A are not limited to the values described in the above-described embodiments and may be changed as appropriate.

The transparent conductive film roll of the present invention is cut by a slitter into pieces having a width of from about 300 to 800 mm and a length of from about 10 to 1000 m. The film is subjected to silver paste printing, dielectric printing or the like, resulting in a transparent electrode for used in a touch panel or electroluminescence panel.

FIG. 11 shows an exemplary analog stylus input touch panel comprising a transparent conductive film obtained by cutting a transparent conductive film roll of the present invention. This touch panel comprises a pair of panel plates having a transparent conductive layer, which are disposed via a spacer so that the transparent conductive layers are opposed to each other, where at least one of the panel plates is a transparent conductive film obtained by cutting a transparent conductive film roll of the present invention.

When a stylus is used to input a character or pattern on the touch panel, a stylus pressure allows the opposing transparent conductive layers to contact each other, resulting in an electrically ON state. Therefore, the position of the stylus can be detected on the touch panel. By detecting the position of the stylus sequentially and accurately, characters can be recognized from the trace of the stylus.

In this case, a transparent conductive film obtained by cutting a transparent conductive film roll of the present invention is provided on a panel plate which contacts a stylus. A surface resistance is substantially uniform in longitudinal and lateral directions of the transparent conductive film. Therefore, a stable touch panel having a small character or pattern recognition deviation rate can be obtained no matter what portion of the transparent conductive film roll is used.

Alternatively, a transparent conductive film obtained by cutting a transparent conductive film roll of the present invention is provided on both panels of an analog stylus input touch panel. A transparent resin sheet is provided via an adhesive agent on a surface of the transparent conductive film on which a conductive layer is not deposited. Thus, a transparent conductive layered sheet for use in a fixed electrode for a touch panel is obtained. By using a fixed electrode made of a resin instead of one made of glass, a touch panel which is light and is difficult to break due to shock can be produced.

The above-described adhesive agent is not particularly limited as long as it has transparency. Preferably examples of the adhesive agent include acrylic-based adhesive agents, silicone-based adhesive agents, rubber-based adhesive agents, and the like. The thickness of the adhesive agent is preferably in the range of from 1 to 100 μm, though it is not particularly limited. When the adhesive agent has a thickness of less than 1 μm, it is difficult to obtain adhesiveness without any practical problem. When the adhesive agent has a thickness of more than 100 μm, the adhesive agent is not preferable in view of productivity.

The transparent resin sheet attached via the adhesive agent is used to provide a mechanical strength equal to that of glass. The transparent resin sheet preferably has a thickness of from 0.05 to 5 mm. When the transparent resin sheet has a thickness of less than 0.05 mm, the mechanical strength thereof is not satisfactory compared to that of glass. When the transparent resin sheet has a thickness of more than 5 mm, the transparent resin sheet is too thick to be suitable for a touch panel. Materials for the above-described transparent plastic film can be used as materials for the transparent resin sheet.

Figure 1:
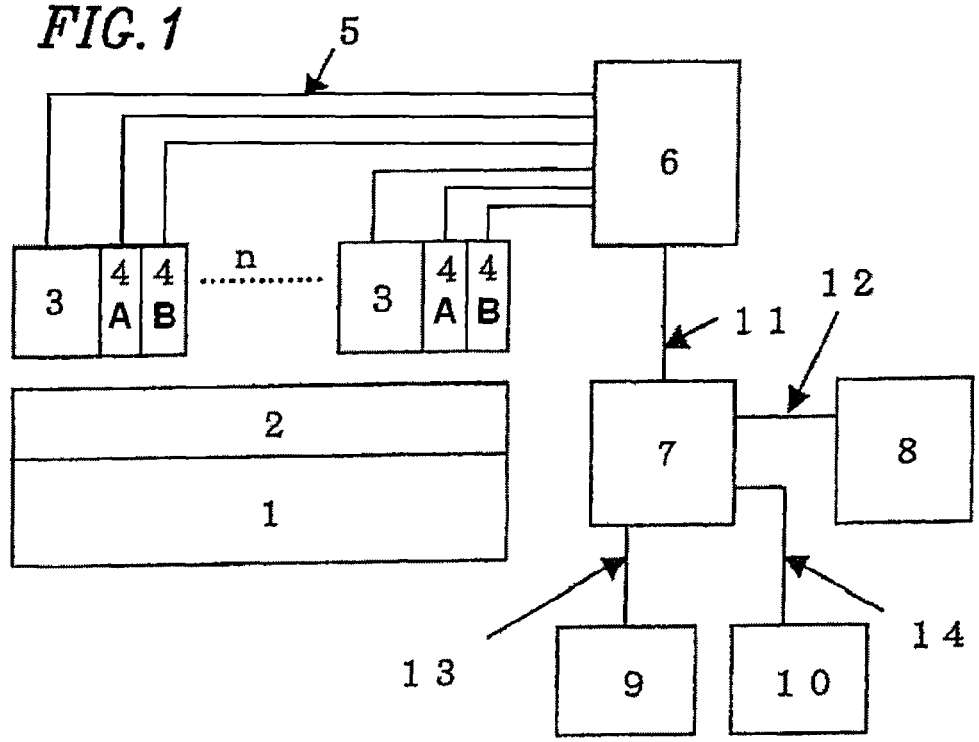
FIG. 1 is a diagram for explaining a configuration of a non-contact surface resistance measuring device.
Figure 2:
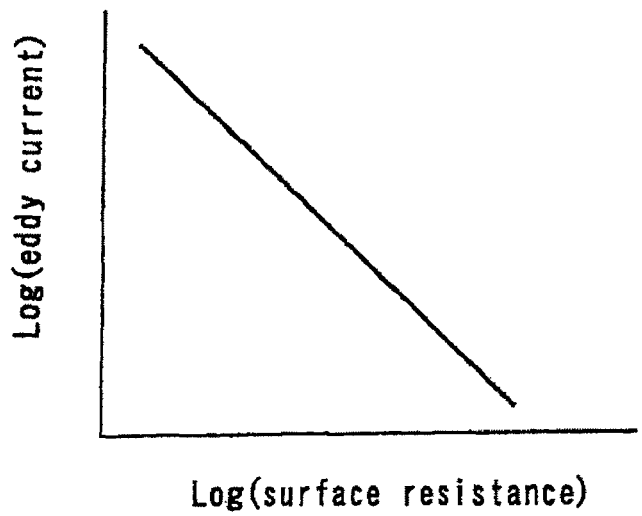
FIG. 2 is a diagram for explaining a calibration curve indicating a relationship between eddy current and surface resistance.
Figure 3:
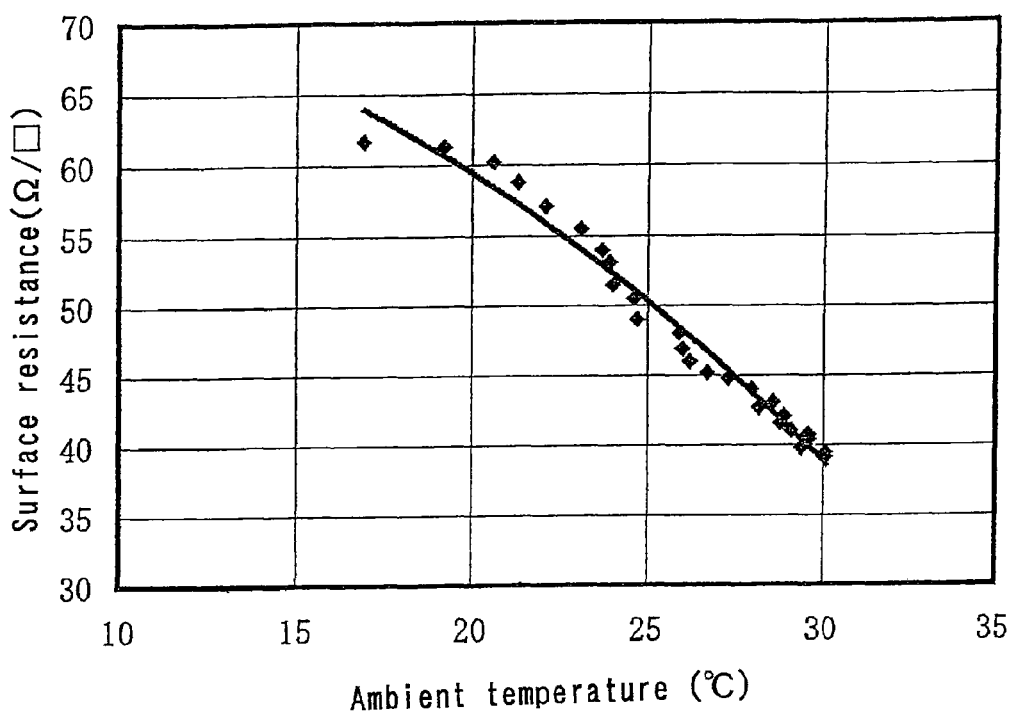
FIG. 3 is a diagram for explaining a calibration curve indicating a relationship between temperature and surface resistance.
Figure 4:
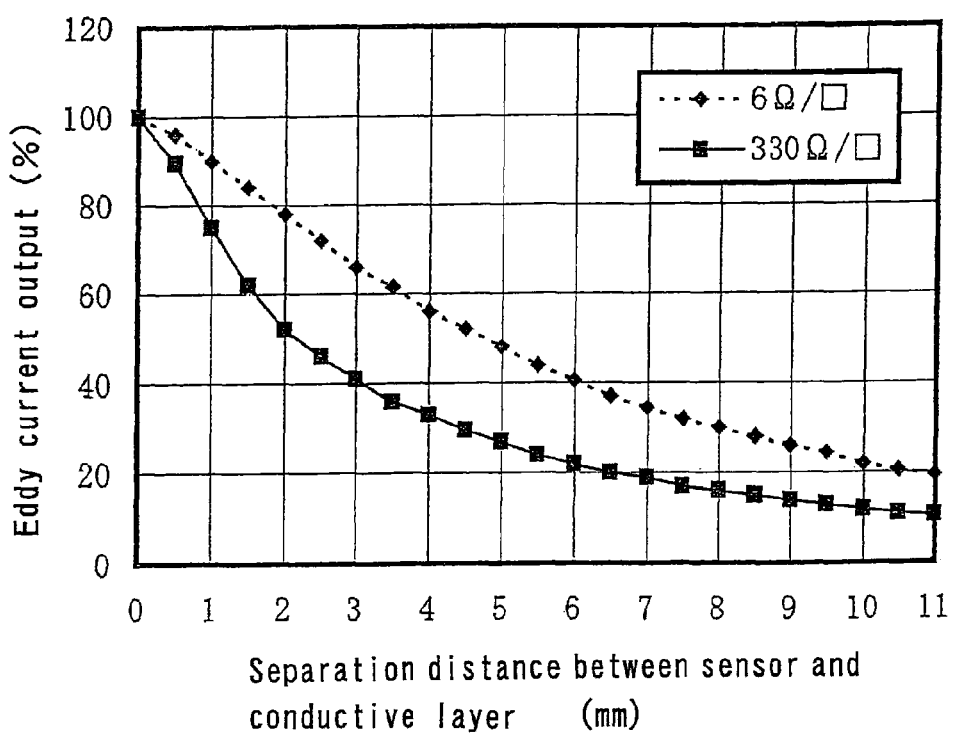
FIG. 4 is a diagram for explaining a calibration curve indicating a relationship between eddy current and separation distance.

DESCRIPTION OF REFERENCE NUMERALS 1 substrate
2 conductive layer
3 eddy current sensor
4A temperature sensor
4B separation distance sensor
5 sensor cable
6 sensor amplifier
7 computer
8 CRT
9 printer
10 alarm device
11 communication cable
12 CRT cable
13 printer cable
14 control cable
15 pattern recognized by a touch panel
16 transparent conductive film
17 plastic film
18 transparent conductive layer
19 glass plate
20 beads

EXAMPLES

Hereinafter, the present invention will be described by way of illustrative examples and comparative examples, though the present invention is not limited to the examples below. Characteristics of transparent conductive film rolls and touch panels obtained in the examples were assessed by a method described below.

(1) The Surface Resistance of a Transparent Conductive Layer

The surface resistance of a transparent conductive layer was measured by a 4-pin probe method using a surface resistance measuring device (Lotest AMCP-T400 manufactured by Mitsubishi Petrochemical) in accordance with JIS-K7194, where measurement was performed at points which were located at a middle portion in a lateral direction of a slit roll of transparent conductive film and points which were located at a distance of 200 mm from the middle portion to the right and left, and these points were separated in 10 m intervals in a longitudinal direction.

Specifically, the surface resistance of the slit roll was measured at 33 points (3 points in the lateral direction×11 points in the longitudinal direction) in a slit roll. The maximum and minimum values of 33 measurement values were represented by Rmax and Rmin, respectively. These values were used to calculate the distribution uniformity D of the surface resistance (=(Rmax−Rmin)/(Rmax+Rmin)). This calculation was performed for a total of 16 slit rolls.

(2) The Pattern Recognition Deviation Rate of a Touch Panel

Five circles having a diameter of 40 mm were written on a touch panel produced as described above using an X-Y plotter (DXY-1150A manufactured by Roland). The tip of a pen of the plotter had a size of 0.8 mmΦ and was made of polyacetal and the pen load was 0.6 N. Signals were read from the silver paste and it was assessed whether or not the circles were correctly recognized. A pattern recognition deviation rate (%) was calculated by $(|r1-r0|/r0) \times 100$, where the length of the major axis of a recognized mark is represented by $r1$ and the diameter of the written circle is represented by $r0$ (=40 mm). The pattern recognition deviation rate was calculated for the five written points. The highest deviation rate was defined as the pattern recognition deviation rate of the touch panel.

Example 1

A sputtering and rolling up device comprising non-contact surface resistance measuring devices incorporating a temperature sensor and a separation distance sensor as shown in FIG. 1 was used and an ITO target (containing 10% by weight of tin oxide, manufactured by Mitsui Mining and Smelting) was employed. Note that the non-contact surface resistance measuring device was provided at three points: a middle portion in a lateral direction of a film; and at a distance of 500 mm from the middle portion to the right and left. A PET film roll having a size of 1300 mm in width, 850 m in length and 188 μm in thickness and having an adhesion-modified layer on one side thereof (A4100 manufactured by Toyo Boseki) was unrolled to provide a substrate. Next, a transparent conductive layer was formed on the adhesion modified surface of the PET film.

Conditions for forming the transparent conductive layer were as follows: a pressure was 0.4 Pa in sputtering; the flow rate of Ar was 200 sccm; and the flow rate of oxygen was 3 sccm. A power of 3 W/cm² was applied to a target using RPG100 (manufactured by Japan ENI). In this case, a positive voltage pulse having a pulse width of 2 μsec and a pulse frequency of 100 kHz was applied to suppress the occurrence of abnormal electric discharge.

Figure 5:
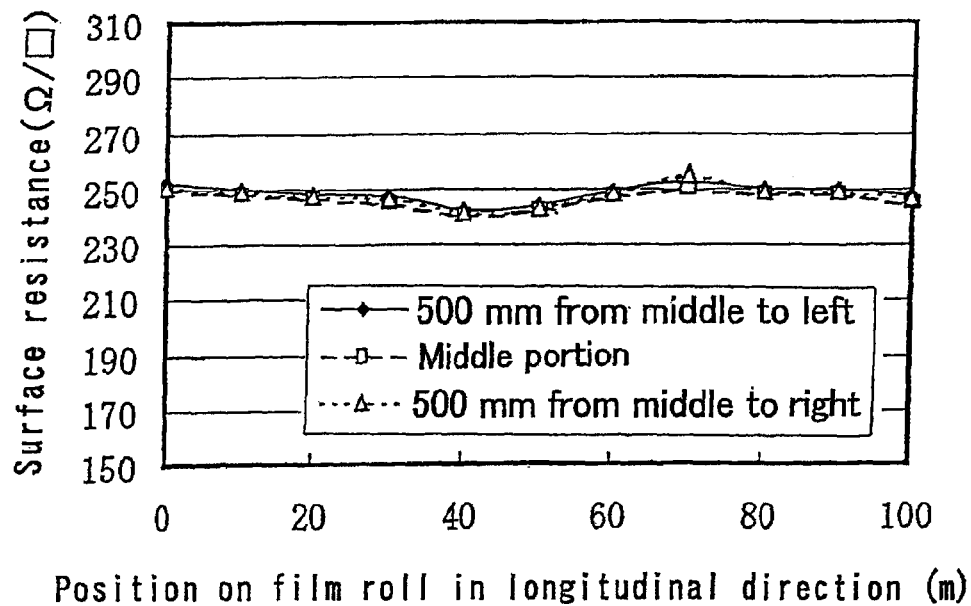
FIG. 5 is a diagram for explaining a surface resistance distribution in a slit roll in Example 1.

Note that the temperature dependency and separation distance dependency of the eddy current sensor were previously measured to prepare a calibration curve. The feed speed of the film and the flow rate of oxygen were adjusted based on the calibration curve while sequentially monitoring the measurement results of the eddy current-type surface resistance measuring device so that the center of the surface resistance of the film was located at 250 Ω/□. The thickness of the transparent conductive layer was from 22 to 27 nm at the time of production of a transparent conductive film roll. Further, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by the eddy current-type surface resistance measuring device are shown in FIG. 5. The distribution uniformity of the surface resistance D of the conductive film was 0.03.

The resultant transparent conductive film roll was slit into 16 slit rolls each having a width of 600 mm and a length of 100 m. The assessment results of the resultant transparent conductive film roll are shown in Table 1.

Figure 11:
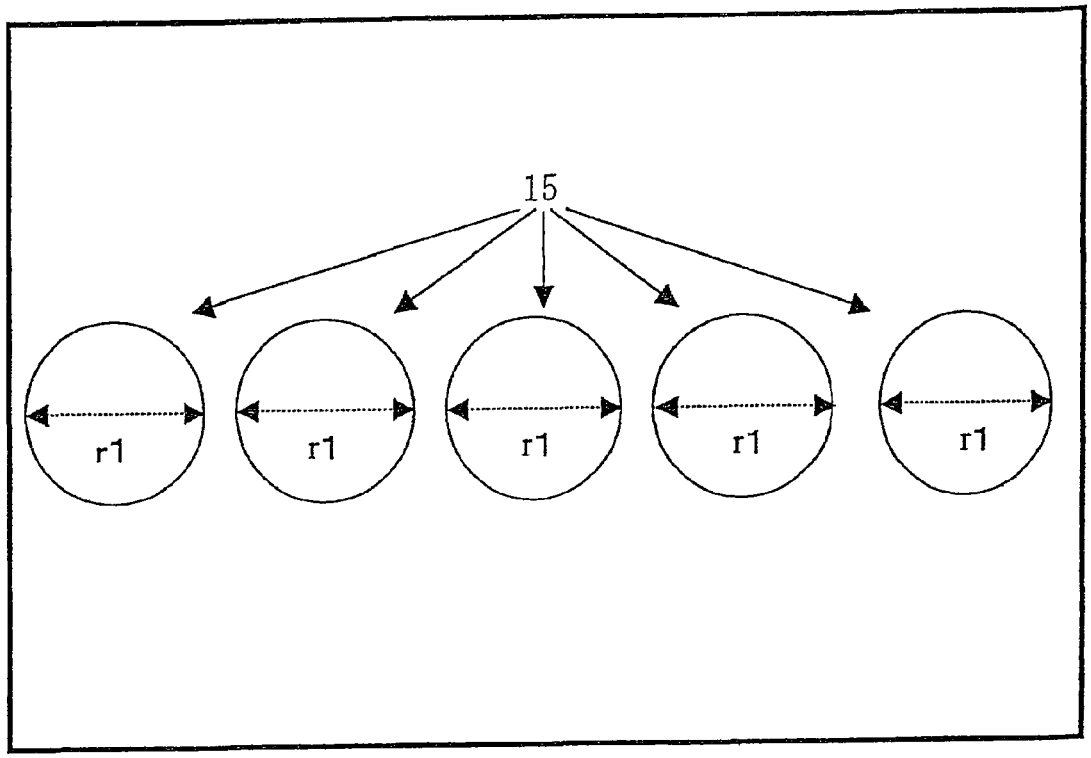
FIG. 11 is a diagram for explaining an output shape of the touch panel of Example 1.
Figure 13:
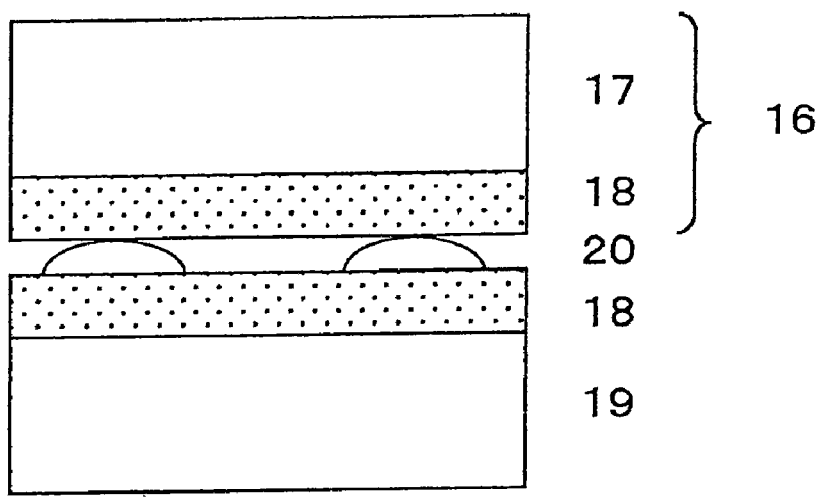
FIG. 13 is a cross-sectional view of the touch panel of Example 1.

A 200 mm×300 mm rectangle of transparent conductive film was cut out from the slit roll of transparent conductive film. The rectangular transparent conductive film was used as one panel plate and a silver paste was printed on opposite ends thereof (sides having a length of 200 mm). A transparent conductive glass (S500 manufactured by Nippon Soda) having a 20-nm thick indium-tin mixed oxide thin film (tin oxide content: 10% by weight), which had been provided on the glass substrate by plasma CVD, was cut into a 200 mm×300 mm rectangle as the other panel plate. A silver paste was printed on opposite ends of the glass panel (sides having a length of 300 mm). The two panel plates were disposed via epoxy beads having a diameter of 30 μm so that the transparent conductive layers faced each other, to produce a touch panel. FIG. 13 shows a cross-sectional view of the resultant touch panel. The result of assessment of the touch panel is shown in Table 2 and FIG. 11.

Example 2

Figure 6:
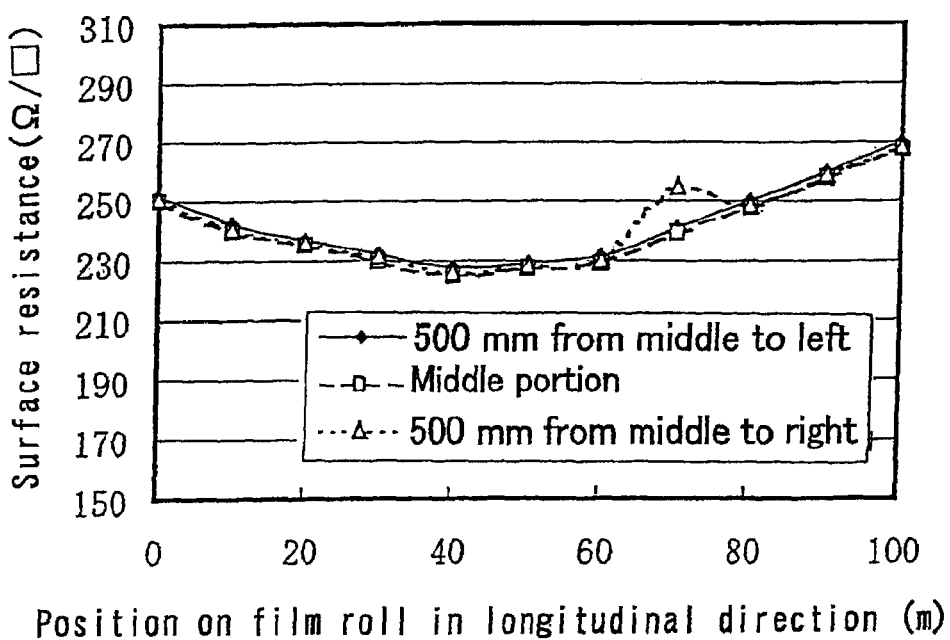
FIG. 6 is a diagram for explaining a surface resistance distribution in a slit roll in Example 2.

A PET film (HC101 manufactured by Toyo Boseki) having a clear hard coating layer having a thickness of 192 μm on one side thereof was used as a plastic film. A transparent conductive film roll and a touch panel were obtained as in Example 1, except that a transparent conductive layer was formed on the other side with respect to the hard coat layer. The results are shown in Tables 1 and 2. As in Example 1, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by an eddy current-type surface resistance measuring device are shown in FIG. 6. The distribution uniformity of the surface resistance D of the conductive film was 0.09.

Example 3

A photopolymerization initiator-containing acrylic resin (Seika Beam EXF-01J manufactured by Dainichiseika Colour & Chemicals Mfg.) was added to a mixed solvent of toluene and MEK (8:2 by weight) to a solid concentration of 50% by weight. The mixture was stirred to afford a homogeneous solution. Thus, application solution A was prepared.

Next, a PET film roll having a size of 1300 mm in width, 850 m in length and 188 μm in thickness and having an adhesion-modified layer on one side thereof (A4100 manufactured by Toyo Boseki) was unrolled. Application solution A was applied to the adhesion modifying layer of the film to a thickness of 5 μm by Mayer bar, followed by drying at 80° C. for 1 min. The film was then irradiated with ultraviolet light using an ultraviolet irradiating device (UB042-5AM-W manufactured by Eyegraphics) (light amount: 300 mJ/cm$^2$) to cure the applied film. In addition, heat treatment was performed at 180° C. for 1 min to reduce the volatile component. The PET film roll having the cured layer on one side thereof was rolled up. The roll was prepared as a substrate.

The PET film roll having the cured layer on one side thereof was used as a substrate as in Example 1 to obtain a transparent conductive film roll and a touch panel, except that a transparent conductive layer was formed on a surface of the cured layer. The results are shown in Tables 1 and 2.

Figure 7:
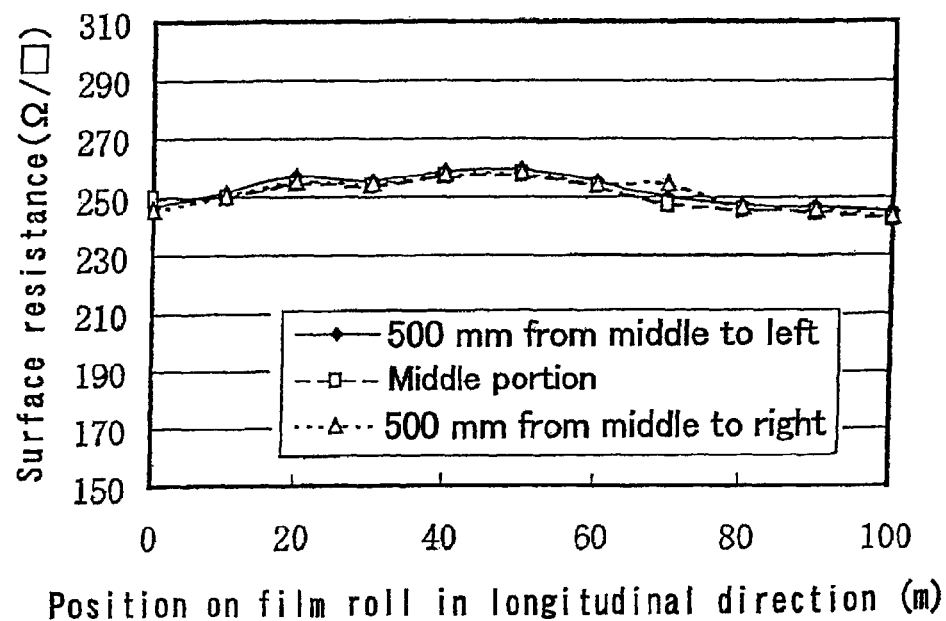
FIG. 7 is a diagram for explaining a surface resistance distribution in a slit roll in Example 3.

As in Example 1, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by an eddy current-type surface resistance measuring device are shown in FIG. 7. The distribution uniformity of the surface resistance D of the conductive film was 0.02.

Example 4

A transparent conductive film roll and a touch panel were produced as in Example 1, except that the feed speed of the film and the flow rate of oxygen were adjusted so that the center of the surface resistance of the film was located at 1000 Ω/□ using a tin-antimony mixed oxide (ATO) target (containing 5% by weight of antimony oxide, manufactured by Mitsui Mining And Smelting) instead of ITO target, and the flow rate of oxygen was changed from 3 sccm to 5 sccm. The results are shown in Tables 1 and 2. The thickness of the transparent conductive layer was from 95 to 110 nm at the time of production of the transparent conductive film roll.

Figure 8:
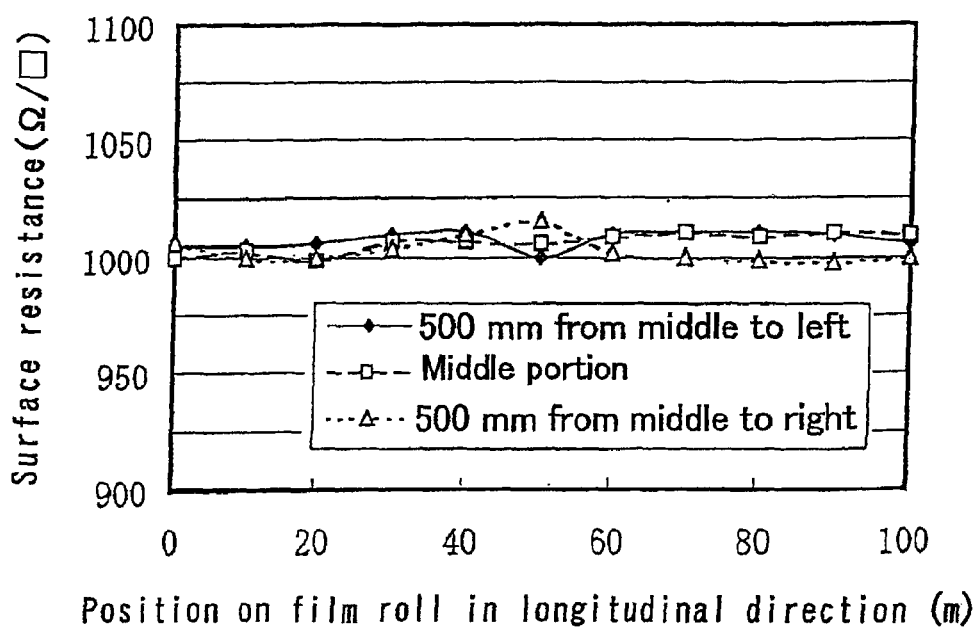
FIG. 8 is a diagram for explaining a surface resistance distribution in a slit roll in Example 4.

As in Example 1, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by an eddy current-type surface resistance measuring device are shown in FIG. 8. The distribution uniformity of the surface resistance D of the conductive film was 0.10.

Example 5

A transparent conductive film roll and a touch panel were produced as in Example 1, except that a non-contact surface resistance measuring device incorporating a temperature sensor and a separation distance sensor is continuously reciprocated in a lateral direction of a conductive film to measure the surface resistance of the conductive film at three points: a middle portion in a lateral direction of the film; and at a distance of 500 mm from the middle portion to the right and left, instead of providing three non-contact surface resistance measuring devices at separated positions on the conductive film of the transparent conductive film. The results are shown in Tables 1 and 2.

Figure 14:
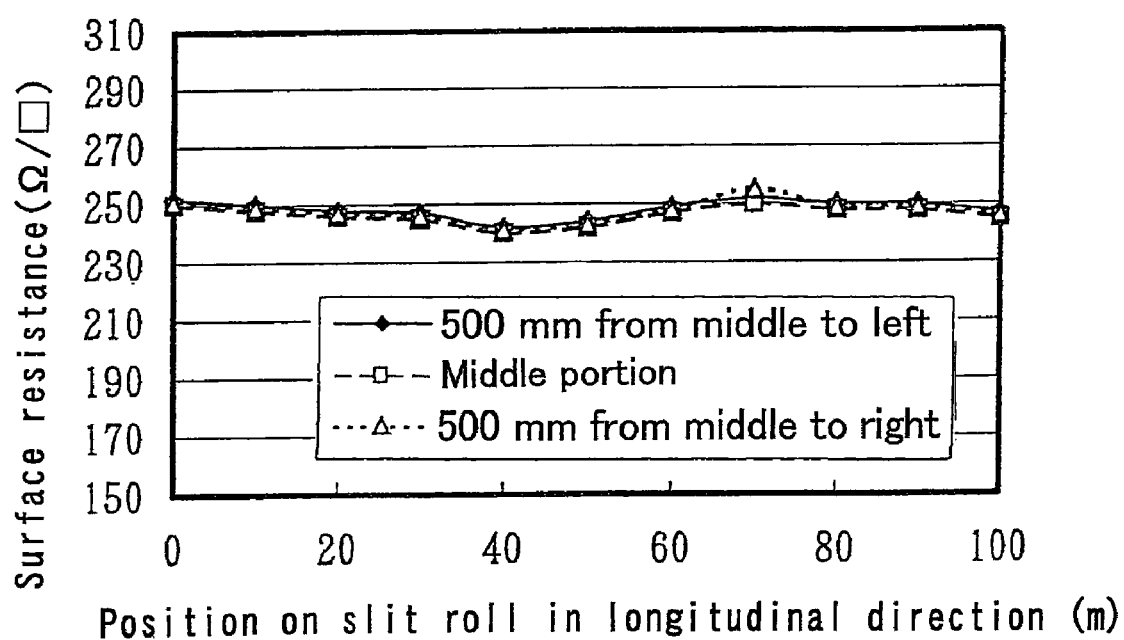
FIG. 14 is a diagram for explaining a surface resistance distribution in a slit roll in Example 5.

As in Example 1, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by an eddy current-type surface resistance measuring device are shown in FIG. 14. The distribution uniformity of the surface resistance D of the conductive film was 0.03.

Comparative Example 1

Figure 12:
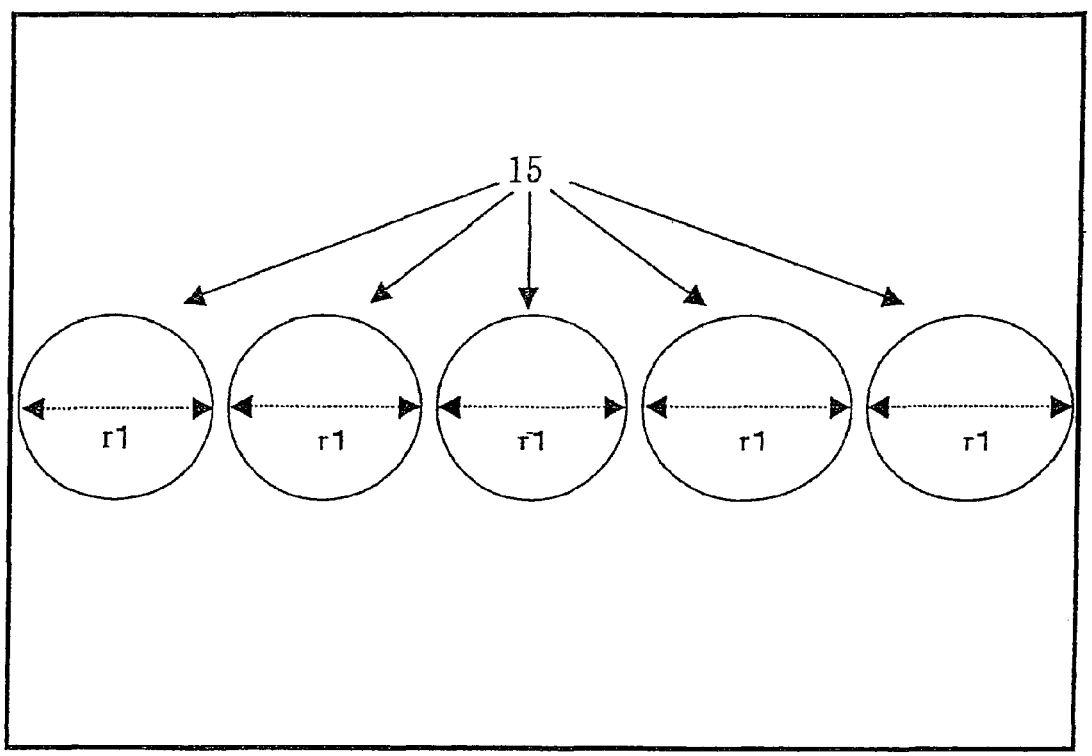
FIG. 12 is a diagram for explaining an output shape of the touch panel of Comparative Example 1.

Comparative Example 1 was the same as Example 1, except that eddy current-type surface resistance measuring devices which did not comprise a temperature sensor and a separation distance sensor were used (provided at a total of three points: a middle portion in a lateral direction of the film; and at a distance of 500 mm from the middle portion to the right and left). The results are shown in Tables 1 and 2 and FIG. 12.

Figure 9:
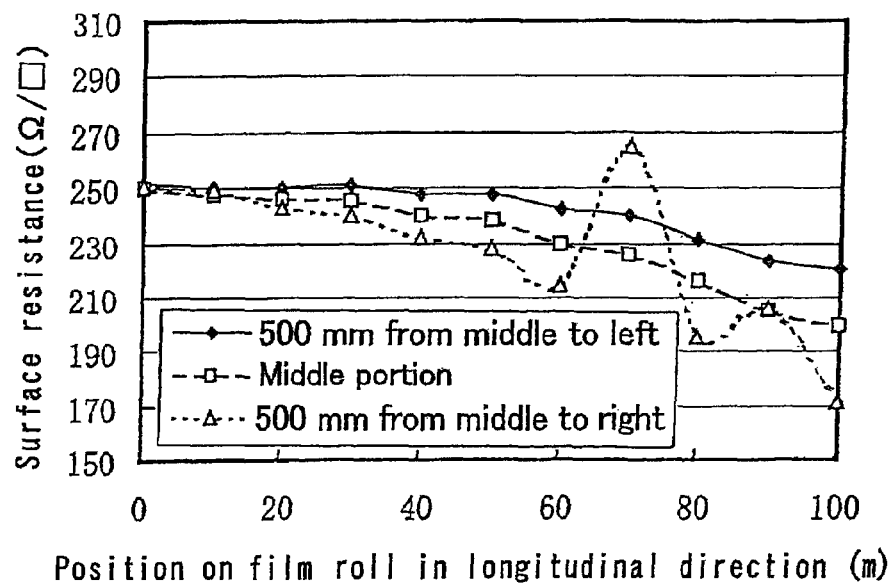
FIG. 9 is a diagram for explaining a surface resistance distribution in a slit roll in Comparative Example 1.

As in Example 1, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by the eddy current-type surface resistance measuring device are shown in FIG. 9. The distribution uniformity of the surface resistance D of the conductive film was 0.22.

Comparative Example 2

Comparative Example 2 was the same as Example 1, except that a monitor for calculating the surface resistance of a film based on a resistance value between two insulation free rolls was used instead of eddy current-type surface resistance measuring devices. The results are shown in Tables 1 and 2.

Figure 10:
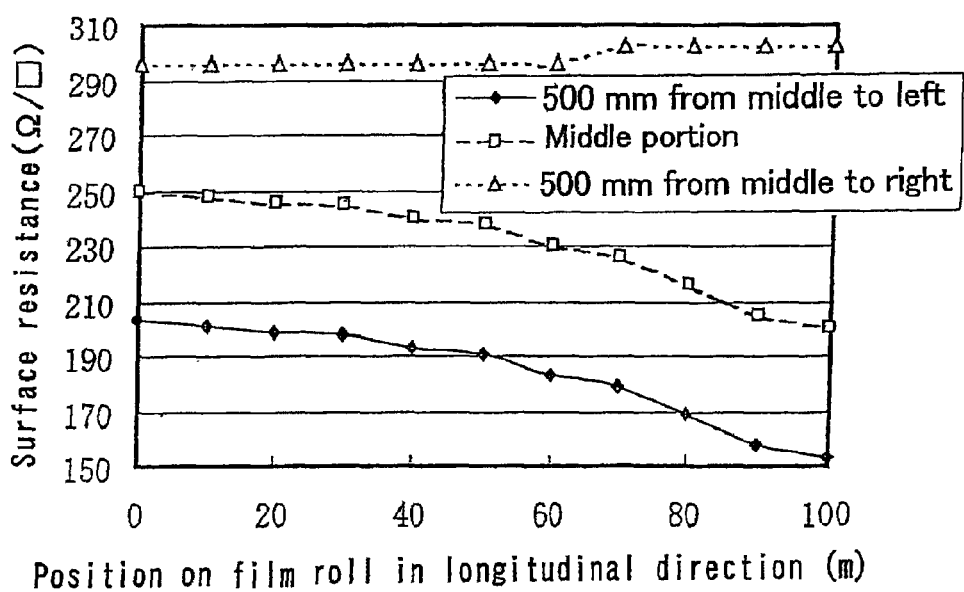
FIG. 10 is a diagram for explaining a surface resistance distribution in a slit roll in Comparative Example 2.

As in Example 1, at the time of production of the transparent conductive film roll, the surface resistance value of the conductive layer was output over 100 m at positions which were located at the middle portion in a lateral direction thereof, positions which were located at a distance of 500 mm from the middle portion to the right, and positions which were located at a distance of 500 mm from the middle portion to the left, and these positions were separated in 10 m intervals in a longitudinal direction thereof. The measurement results by an eddy current-type surface resistance measuring device are shown in FIG. 10. The distribution uniformity of the surface resistance D of the conductive film was 0.33.

TABLE 1

| Slit roll No. | Surface resistance distribution uniformity D of conductive film | | | | | | |
|---|---|---|---|---|---|---|---|
| | Example 1 | Example 2 | Example 3 | Example 4 | Example 5 | Comparative Example 1 | Comparative Example 2 |
| 1 | 0.03 | 0.09 | 0.02 | 0.10 | 0.03 | 0.22 | 0.33 |
| 2 | 0.03 | 0.11 | 0.04 | 0.12 | 0.03 | 0.23 | 0.32 |
| 3 | 0.05 | 0.05 | 0.06 | 0.16 | 0.05 | 0.26 | 0.29 |
| 4 | 0.02 | 0.12 | 0.02 | 0.17 | 0.02 | 0.34 | 0.25 |
| 5 | 0.06 | 0.06 | 0.05 | 0.12 | 0.06 | 0.23 | 0.33 |
| 6 | 0.08 | 0.08 | 0.07 | 0.18 | 0.08 | 0.25 | 0.29 |
| 7 | 0.03 | 0.13 | 0.09 | 0.12 | 0.03 | 0.36 | 0.36 |
| 8 | 0.05 | 0.15 | 0.02 | 0.16 | 0.05 | 0.24 | 0.28 |
| 9 | 0.04 | 0.06 | 0.09 | 0.18 | 0.04 | 0.21 | 0.26 |
| 10 | 0.08 | 0.16 | 0.10 | 0.11 | 0.08 | 0.36 | 0.31 |
| 11 | 0.03 | 0.06 | 0.09 | 0.11 | 0.03 | 0.25 | 0.30 |
| 12 | 0.05 | 0.13 | 0.12 | 0.17 | 0.05 | 0.22 | 0.29 |
| 13 | 0.06 | 0.05 | 0.08 | 0.12 | 0.06 | 0.23 | 0.27 |
| 14 | 0.03 | 0.08 | 0.09 | 0.09 | 0.03 | 0.28 | 0.25 |
| 15 | 0.08 | 0.03 | 0.10 | 0.09 | 0.08 | 0.23 | 0.24 |
| 16 | 0.05 | 0.12 | 0.02 | 0.02 | 0.05 | 0.21 | 0.26 |

TABLE 2

| | Pattern recognition deviation rate (%) |
|---|---|
| Example 1 | 0.32 |
| Example 2 | 0.86 |
| Example 3 | 0.45 |
| Example 4 | 0.76 |
| Example 5 | 0.32 |
| Comparative Example 1 | 2.51 |
| Comparative Example 2 | 3.68 |

According to the above-described results, the following was found.

In Examples 1 to 5, the surface resistance distribution of the transparent conductive layer in the slit roll of the transparent conductive film is uniform in both the longitudinal and lateral directions. Therefore, for example, input patterns can be accurately recognized by the touch panel produced from the slit roll of the transparent conductive film of Example 1.

In contrast, the surface resistance distribution of the transparent conductive layer of Comparative Example 1 had insufficient uniformity in the longitudinal direction and that of Comparative Example 2 had in sufficient uniformity in the lateral direction. Therefore, for example, the touch panel produced from the slit roll of the transparent conductive film of Comparative Examples 1 or 2 had a high pattern recognition deviation rate and was thus inadequate.

INDUSTRIAL APPLICABILITY

A transparent conductive film roll having quality, such as surface resistance or the like, which is uniform in longitudinal and lateral directions thereof, is obtained, leading to excellent functional stability, such as less character or pattern recognition deviation rate or the like, when the transparent conductive film roll is used in a final product, such as a touch panel or the like.

The invention claimed is:

1. A method for producing a transparent conductive film roll having a width of from 300 mm to 1300 mm and a length of from 10 m to 1000 m, and having a transparent conductive layer on at least one side thereof using a rolled-up film forming device, wherein the rolled-up film forming device has a non-contact surface resistance measuring device therewithin, a surface resistance of the transparent conductive layer is sequentially measured in line at a plurality of positions in each of longitudinal and lateral directions of the film while forming the transparent conductive layer, and conditions for forming the transparent conductive layer are regulated so that the surface resistance thereof is uniformly distributed.

2. A transparent conductive film roll production method according to claim 1, wherein the non-contact surface resistance measuring device mainly comprises an eddy current generating section which is placed at a predetermined distance from the transparent conductive layer, faces the transparent conductive layer and flows an eddy current in the transparent conductive layer, an eddy current detecting section which is separated from the transparent conductive layer and detects the eddy current flowing through the transparent conductive layer, a temperature detecting section which detects a temperature of the eddy current generating section or the eddy current detecting section, and a calculating means which calculates the surface resistance of the transparent conductive layer based on a result of detection by the eddy current detecting section and a result of detection by the temperature detecting section where a voltage applied to the eddy current generating section is constant, wherein when the result of detection by the temperature detecting section is deviated from a reference temperature, the calculating means calculates an amount of an increase or decrease in the eddy current caused by the deviation from the reference temperature and adds or subtracts the amount of the increase or decrease in the eddy current to or from the result of detection by the eddy current detecting section to correct the value of the eddy current and calculates the surface resistance of the transparent conductive layer based on the corrected value of the eddy current.

3. A transparent conductive film roll production method according to claim 1, wherein a plurality of non-contact surface resistance measuring devices are provided in the lateral direction of the film.

4. A transparent conductive film roll production method according to claim 1, wherein the non-contact surface resistance measuring device is continuously reciprocated in the lateral direction of the film.

* * * * *